United States Patent
Mantese et al.

(10) Patent No.: US 11,292,198 B2
(45) Date of Patent: Apr. 5, 2022

(54) SITU MONITORING OF STRESS FOR ADDITIVELY MANUFACTURED COMPONENTS

(71) Applicant: Hamilton Sundstrand Corporation, Charlotte, NC (US)

(72) Inventors: Joseph V. Mantese, Ellington, CT (US); Abhijit Chakraborty, West Hartford, CT (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 384 days.

(21) Appl. No.: 16/166,931

(22) Filed: Oct. 22, 2018

(65) Prior Publication Data
US 2020/0122401 A1   Apr. 23, 2020

(51) Int. Cl.
*B29C 64/393*   (2017.01)
*B29C 64/264*   (2017.01)
*G01L 1/25*   (2006.01)
*G01N 23/20008*   (2018.01)
*B33Y 10/00*   (2015.01)
(Continued)

(52) U.S. Cl.
CPC .......... *B29C 64/393* (2017.08); *B29C 64/264* (2017.08); *G01L 1/25* (2013.01); *G01N 23/20008* (2013.01); *B33Y 10/00* (2014.12); *B33Y 40/00* (2014.12); *B33Y 50/02* (2014.12); *B33Y 70/00* (2014.12); *G01N 2223/056* (2013.01); *G01N 2223/607* (2013.01); *G01N 2223/646* (2013.01)

(58) Field of Classification Search
CPC ................................... B29C 64/393
See application file for complete search history.

(56) References Cited

U.S. PATENT DOCUMENTS 9,981,341 B2   5/2018   Mazumder et al.
9,999,924 B2   6/2018   Dave et al.
(Continued)

FOREIGN PATENT DOCUMENTS

EP   3269535 A1   1/2018
EP   3323617 A1 *   5/2018   .......... B29C 64/245
(Continued)

OTHER PUBLICATIONS

European Search Report Issued in European Application No. 19204508.6 dated Mar. 4, 2020; 7 Pages.

*Primary Examiner* — Timothy Kennedy
*Assistant Examiner* — Asha A Thomas
(74) *Attorney, Agent, or Firm* — Cantor Colburn LLP

(57) ABSTRACT

A material deposition process including in situ sensor analysis of a component in a formation state is provided. The material deposition process is implemented in part by a sensor device of an additive manufacturing machine producing the component. The material deposition process includes sensing, by the sensing device, in situ physical properties of an area of interest of the component during a three-dimensional object production. Compliance to specifications or defects are then detected in the in situ physical properties with respect to pre-specified material requirements. The defects are analyzed to determine corrective actions, and an updated three-dimensional object production, which includes the corrective actions, is implemented to complete the component.

7 Claims, 3 Drawing Sheets

(51) Int. Cl.
*B33Y 40/00* (2020.01)
*B33Y 50/02* (2015.01)
*B33Y 70/00* (2020.01)

(56) References Cited

U.S. PATENT DOCUMENTS

| | | | |
|---|---|---|---|
| 10,502,701 B2* | 12/2019 | Lobastov | B22F 10/20 |
| 2016/0151978 A1* | 6/2016 | Lin | B29C 64/106 |
| | | | 264/40.7 |
| 2016/0236414 A1 | 8/2016 | Reese et al. | |
| 2016/0258256 A1* | 9/2016 | Nguyen | B22F 3/10 |
| 2017/0001379 A1* | 1/2017 | Long | B29C 64/393 |
| 2017/0023499 A1 | 1/2017 | Mitchell | |
| 2017/0274599 A1* | 9/2017 | Kitamura | B33Y 50/02 |
| 2017/0312821 A1 | 11/2017 | Defelice et al. | |
| 2018/0001565 A1* | 1/2018 | Hocker | G01N 23/223 |
| 2018/0071987 A1* | 3/2018 | Tsumuraya | B22F 10/20 |
| 2018/0126670 A1 | 5/2018 | Dehghanniri et al. | |

FOREIGN PATENT DOCUMENTS

| | | |
|---|---|---|
| EP | 3323617 A1 | 5/2018 |
| WO | 2017015115 A1 | 1/2017 |

* cited by examiner

SITU MONITORING OF STRESS FOR ADDITIVELY MANUFACTURED COMPONENTS

BACKGROUND

Conventional additive manufacturing processes have limited or no closed loop controls and, therefore, rely on final material property assessments of a finished manufactured part or product. Specifically, conventional additive manufacturing utilizes post deposition analysis to provide these assessments.

BRIEF DESCRIPTION

In accordance with one or more embodiments, a material deposition process including in situ sensor analysis of a component in a formation state is provided. The material deposition process is implemented in part by an X-ray source and an X-ray detector of an additive manufacturing machine producing the component. The material deposition process includes sensing, by the X-ray source and the X-ray detector, in situ physical properties of an area of interest of the component during a three-dimensional object production. Compliance to specifications or defects are then detected in the in situ physical properties with respect to pre-specified material requirements. The defects are analyzed to determine corrective actions, and an updated three-dimensional object production, which includes the corrective actions, is implemented to complete the component.

In accordance with one or more embodiments or the material deposition process embodiment above, the material deposition process can include implementing the three-dimensional object production of the component according to a computer design file.

In accordance with one or more embodiments or any of the material deposition process embodiments above, the material deposition process can include feeding forward and back the corrective actions to the three-dimensional object production in real time to generate the updated three-dimensional object production.

In accordance with one or more embodiments or any of the material deposition process embodiments above, the at least one sensing device can include an X-ray source and X-ray detector that together acquire a full or partial X-ray diffraction signal or pattern that is analyzed to determine the in situ physical properties.

In accordance with one or more embodiments or any of the material deposition process embodiments above, the in situ physical properties can potentially include: hardness, local strain, yield strength, density, crystallite size, porosity, defect density, crystalline orientation, texture, and compositional variation.

In accordance with one or more embodiments or any of the material deposition process embodiments above, a compute device can include a processor executing software to provide one or more process modeling, toolpath planning, defect detection, layer defect detection, part defect detection, feedback control, scan path planning, decision making, and process sensing operations for detecting the defects.

In accordance with one or more embodiments or any of the material deposition process embodiments above, a compute device can include a database storing and providing the pre-specified material requirements and a computer design file for detecting the defects and implementing the three-dimensional object production.

In accordance with one or more embodiments, a system for implementing a three-dimensional object production of a component via an additive manufacturing is provided. The system includes an additive manufacturing machine including an X-ray source and an X-ray detector. The system also includes a compute device including a processor and a memory. The compute device is communicatively coupled to the additive manufacturing machine and the X-ray source and the X-ray detector. The additive manufacturing machine and the compute device provide in situ sensor analysis of the component while in a formation state during a material deposition process of the additive manufacturing by sensing, by the X-ray source and the X-ray detector, in situ physical properties of an area of interest of the component during a three-dimensional object production. Compliance to specifications or defects are then detected in the in situ physical properties with respect to pre-specified material requirements. The defects are analyzed to determine corrective actions, and an updated three-dimensional object production, which includes the corrective actions, is implemented to complete the component.

In accordance with one or more embodiments or the system embodiment above, the three-dimensional object production of the component can be implemented according to a computer design file.

In accordance with one or more embodiments or any of the system embodiments above, the compute device can feed forward and back the corrective actions to the three-dimensional object production in real time to generate the updated three-dimensional object production.

In accordance with one or more embodiments or any of the system embodiments above, the at least one sensing device can include an X-ray source and X-ray detector that together acquire a full or partial X-ray diffraction signal or pattern that is analyzed to determine the in situ physical properties.

In accordance with one or more embodiments or any of the system embodiments above, the in situ physical properties can include hardness, local strain, yield strength, density, crystallite size, porosity, defect density and compositional variation.

In accordance with one or more embodiments or any of the system embodiments above, a compute device can include a processor executing software to provide one or more process modeling, toolpath planning, defect detection, layer defect detection, part defect detection, feedback control, scan path planning, decision making, and process sensing operations for detecting the defects.

In accordance with one or more embodiments or any of the system embodiments above, a compute device can include a database storing and providing the pre-specified material requirements and a computer design file for detecting the defects and implementing the three-dimensional object production.

BRIEF DESCRIPTION OF THE DRAWINGS

The following descriptions should not be considered limiting in any way. With reference to the accompanying drawings, like elements are numbered alike.

and

Figure 3:
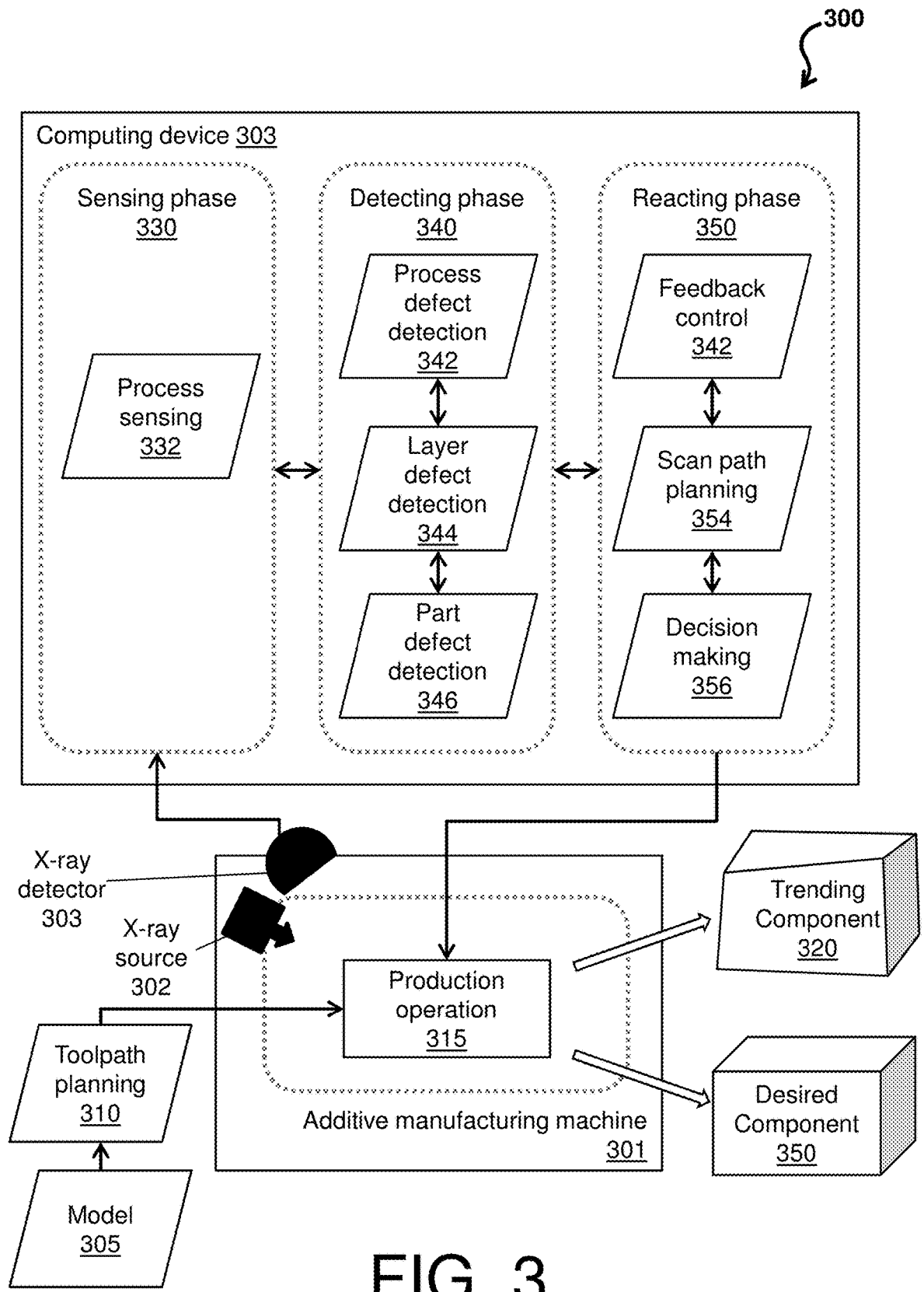

FIG. 3 depicts a schematic flow according to one or more embodiments.

DETAILED DESCRIPTION

A detailed description of one or more embodiments of the disclosed apparatus and method are presented herein by way of exemplification and not limitation with reference to the Figures.

Turning now to an overview of technologies that are more specifically relevant to aspects of the invention, as discussed above, conventional additive manufacturing is rapidly emerging means of flexible manufacturing. However, part-to-part variation, non-uniformity of properties across finished manufactured parts or products, and local or extended defects are significant concerns in utilizing conventional additive manufacturing for high volume production. Most conventional additive manufacturing processes have limited or no closed loop control. Therefore, post deposition analysis is employed to assess only final material properties of the finished manufactured part or product relative to pre-determined materials requirements. Further, post deposition analysis does not allow a manufacturer to change or adapt properties during manufacturing.

Turning now to an overview of the aspects of the invention, one or more embodiments of the invention address the above-described shortcomings of the conventional additive manufacturing by providing, via a system, a method, and/or an apparatus (referred to as a system, herein, for brevity), material deposition processes including in situ sensor analysis. The in situ sensor analysis of the material deposition processes extracts physical properties of a component in a formation state during its additive manufacturing. The material deposition processes, then, feed forward and back these physical properties to the additive manufacturing for continuous adaptability. The technical effects and benefits of embodiments of the material deposition processes herein include determining these physical properties during the formation state of the component and, thus, enabling corrective actions, such as altering additive manufacturing depositions, to achieve pre-specified material requirements.

Figure 1:
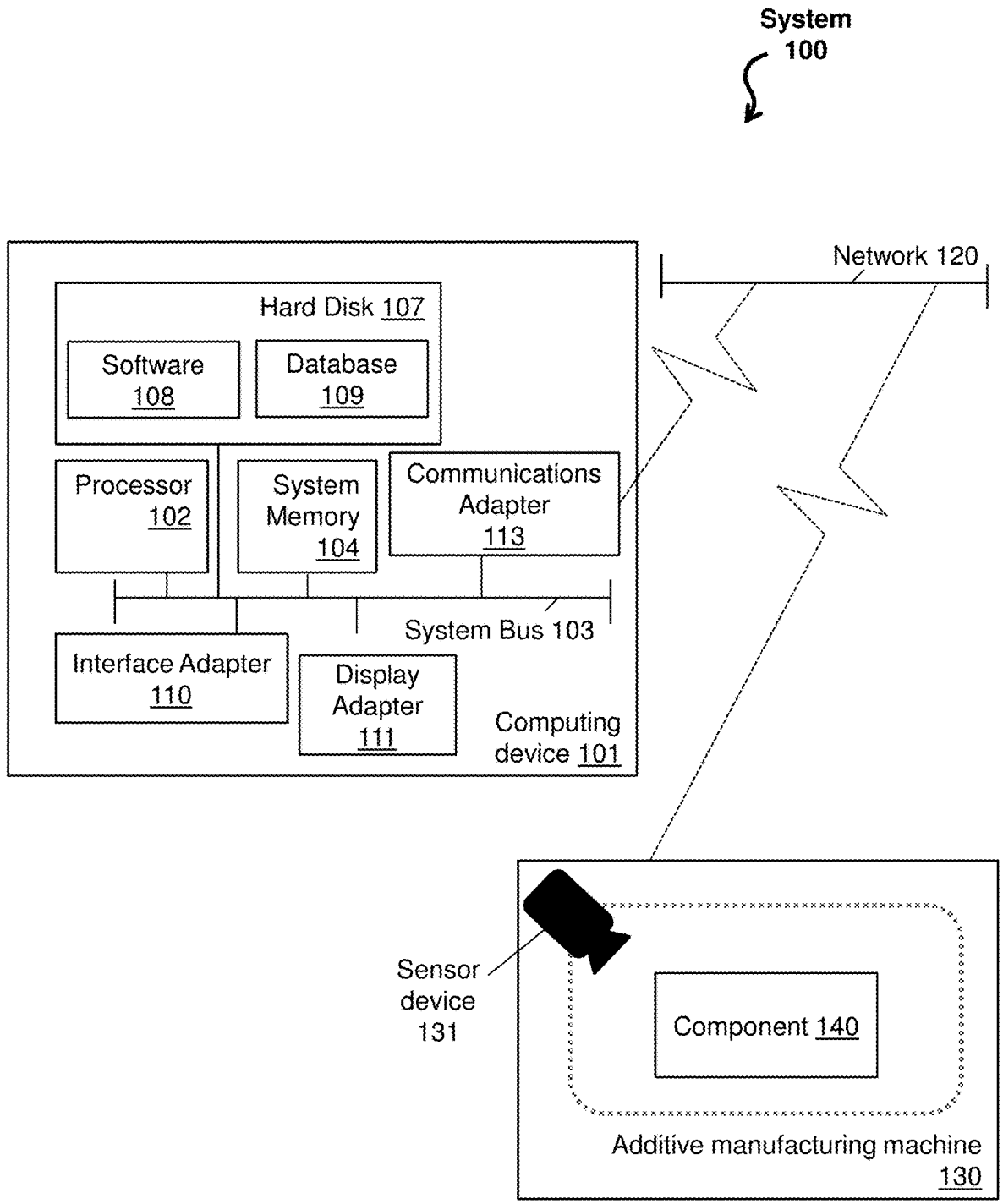
FIG. 1 depicts a system according to one or more embodiments.

Turning now to FIG. 1, a system 100 for implementing the teachings herein is shown in according to one or more embodiments. The system 100 implements material deposition processes including in situ sensor analysis.

In this embodiment, the system 100 includes a compute device 101. The compute device 101 can be an electronic, computer framework comprising and/or employing any number and combination of computing device and networks utilizing various communication technologies, as described herein. The compute device 101 can be easily scalable, extensible, and modular, with the ability to change to different services or reconfigure some features independently of others.

The compute device 101 has a processor 102, which can include one or more central processing units (CPUs). The processor 102, also referred to as a processing circuit, microprocessor, computing unit, is coupled via a system bus 103 to a system memory 104 and various other components. The system memory 104 includes read only memory (ROM) and random access memory (RAM). The ROM is coupled to the system bus 103 and may include a basic input/output system (BIOS), which controls certain basic functions of the system 100. The RAM is read-write memory coupled to the system bus 103 for use by the processor 102.

The compute device 101 includes a hard disk 107, which is an example of a tangible storage medium readable executable by the processor 102. The hard disk 107 stores software 108 and database 109. The software 108 is stored as instructions for execution on the system 100 by the processor 102 (to perform process, such as the process flows of FIGS. 2-3). The database 109 includes a set of values of qualitative or quantitative variables organized in various data structures to support and be used by operations of the software 108. Examples of operations provided by the software 108 include process modeling, toolpath planning, defect detection, layer defect detection, part defect detection, feedback control, scan path planning, decision making, and process sensing. Examples of items stored on the database 109 include computer design files, pre-specified material requirements, assessment models, assessment algorithms, and the like.

The compute device 101 includes one or more adapters (e.g., hard disk controllers, network adapters, graphics adapters, etc.) that interconnect and support communications between the processor 102, the system memory 104, the hard disk 107, and other components of the translation system 100 (e.g., peripheral and external devices). In one or more embodiments of the present invention, the one or more adapters can be connected to one or more 110 buses that are connected to the system bus 103 via an intermediate bus bridge, and the one or more 110 buses can utilize common protocols, such as the Peripheral Component Interconnect (PCI).

The compute device 101 includes an interface adapter 110 interconnecting a keyboard, a mouse, a speaker, a microphone, etc. to the system bus 103. The compute device 101 includes a display adapter 111 interconnecting the system bus 103 to a display. The display adapter 111 (and/or the processor 102) can include a graphics controller to provide graphics performance, such as a display and management of a graphic user interface. A communications adapter 113 interconnects the system bus 103 with a network 120 enabling the translation system 100 to communicate with other systems, devices, data, and software, such as an additive manufacturing machine 130.

The system 100 includes the additive manufacturing machine 130, which further comprises at least one sensor device 131, along with a processor, a memory, tool/feeder, and other machining parts that are not shown for brevity. Note that while shown as separate mechanisms communicating across the network 120, in accordance with one or more embodiment, the compute device 101 and the additive manufacturing machine 130 can be integrated into a single apparatus.

The additive manufacturing machine 130 is configured to manufacture a component 140 via the material deposition processes including in situ sensor analysis. In general, additive manufacturing is a three-dimensional object production process utilizing computer design file. In this regard, a variety of materials, ranging from polymer composites, metals, ceramics, food, foams, gels, alloys, and the like, are deposited by a tool or feeder according to the computer design file and heated by an electric beam to set the material in place. The location of the deposited materials as the tool or feeder moves according to the computer design file is referred to as a tool path.

The at least one sensor device 131 can be any device including transducer and/or a generator. In general, the transducer of the sensor device 131 can be any detector converts variations in a physical quantity into an electrical signal. Examples of physical quantities can include such as local strain, yield strength, density, crystallite size, porosity, defect density, crystalline orientation, texture, compositional variation, temperature, local porosity, optical density, reflectance (e.g., note that because some of these quantities are difficult to extract, the sensor device 131 provides added benefits for in situ analysis). The generator (also known as a source) of the sensor device 131 can be any mechanism that, in response to electrical signals, generates a wave, which itself is detectable or a reflection thereof is detectable by the transducer. The at least one sensor device 131 can also communicate via any interface, such as a controller area network (CAN), a local interconnect network (LIN), a direct I/O interface, an analog to digital (A/D) interface, a digital to analog (D/A) interface, or any other interface specific to the input, to the compute device 101 via the network 130, along with a processor, a memory, and machining parts of the additive manufacturing machine 130. Note that the at least one sensor device 131 is representative of one or more sensors of the same or varying type, each of which is capable of extracting physical properties of the component 140 in a formation state during its additive manufacturing. Example of the at least one sensor device 131 include, but are not limited to, an X-ray, ultra-violet, visible light, near-infrared, short-wave infrared, mid-wavelength infrared, long-wavelength infrared, and terahertz sensors, cameras, and detectors. In accordance with one or more embodiments, the at least one sensor device 131 includes an X-ray source and X-ray detector that together acquire a full or partial X-ray diffraction signal or pattern that is analyzed to determine the in situ physical properties. Further, the X-ray source and the X-ray detector can be directed to detect a small portion of the full X-ray diffraction pattern, such that a single peak with a particular intensity and width representing the detection.

Thus, as configured in FIG. 1, the operations of the software 108, the database 109, and the additive manufacturing machine 130 (e.g., the system 100) are necessarily rooted in the computational ability of the processors therein to overcome and address the herein-described shortcomings of the conventional additive manufacturing. In this regard, the software 108 and the data 109 improve manufacturing operations of the additive manufacturing machine 130 by reducing and eliminating errors in manufacturing, part-to-part variation, non-uniformity of properties, and local or extended defects for high volume production.

Figure 2:
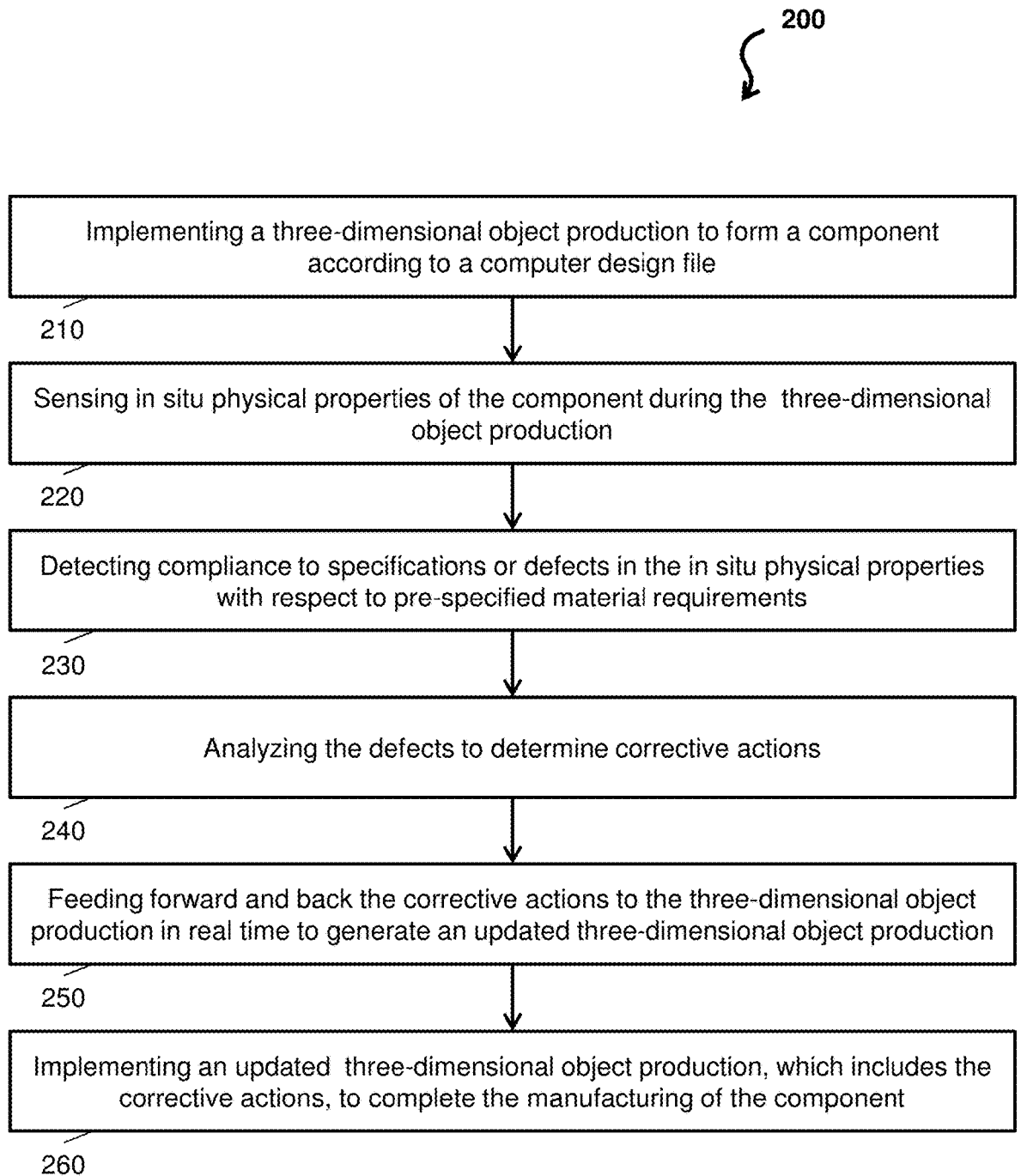
FIG. 2 depicts a process flow according to one or more embodiments.

FIG. 2 depicts a process flow 200 of according to one or more embodiments. The process flow 200 is an example operation of implementing material deposition processes including in situ sensor analysis of the component 140 in a formation state during its additive manufacturing by the system 100.

The process flow 200 being at block 210, where the system 100 implements a material deposition process to form the component 140 according to a computer design file. In this regard, the additive manufacturing machine 130 can receive the computer design file from the database 109 of the compute device 101 and begin three-dimensional object production of the component 140.

At block 220, the system 100 senses in situ physical properties of the component 140 during the material deposition process. In accordance with one or more embodiments, the at least one sensor device 131 is an X-ray detector that acquires an X-ray diffraction (XRD) pattern while the component 140 is in a formation state (prior to completion). Various parameters of the XRD pattern are analyzed by the software 108 of the compute device 101 to determine the in situ physical properties or material parameters, such as hardness, local strain, yield strength, density, crystallite size, porosity, defect density and compositional variation (among other properties). The XRD pattern can be taken from any area of interest of the component 140, as directed by the compute device 101.

At block 230, the system 100 detects compliance to specifications or defects of the in situ physical properties with respect to pre-specified material requirements. In this regard, the compute device 101 can compare the pre-specified material requirements of the database 109 to the in situ physical properties and determine if any defects are present. At block 240, all defects are analyzed by the system 100 (e.g., by the software 108 of the compute device 101) to determine whether corrective actions need to be taken and what those corrective action should be.

At block 250, the system 100 feeds forward and back the corrective actions to the material deposition process in real time for continuous adaptability, thereby updating the material deposition process (e.g., altering additive manufacturing depositions) to account for the defects and achieve pre-specified material requirements. At block 260, the system 100 implements the material deposition process with the corrective actions to complete the manufacturing of the component 140.

Turning now to FIG. 3, a schematic flow 300 is depicted according to one or more embodiments. The schematic flow 300 is an example operation of implementing in situ monitoring of stress for a component (including in situ and post situ process controls) by a system. The schematic flow 300 is executed by an additive manufacturing machine 301 comprising an X-ray source 302 and an X-ray detector 303 (e.g., an example of the sensor device 131 of FIG. 1) and a computing device 304. To the extent that these items overlap with the above system 100, further description is not provided for the sake of brevity.

In general, the schematic flow 300 depicts a model 305 and a toolpath planning being received by the additive manufacturing machine 301 and utilized in a production operation 315 to produce a component. Due to any number of factors during the production operation 315, the additive manufacturing machine 301 may produce a trending component 320. The trending component 320 is note desired as a final component.

As shown in FIG. 3, the computing device 304 executes a sensing phase 330 through a process sensing 322. The process sensing 322 includes receiving physical properties of the component while the component is in a formation state. The X-ray source 302 generates X-rays so that an XRD pattern can be taken from any area of interest by the X-ray detector 303. The physical properties are communicated by the X-ray detector 303 of the additive manufacturing machine 301, which is performing the in situ monitoring. The process sensing 322 further include comparing pre-specified material requirements to the in situ physical properties to provide comparison information. The sensing phase 330 and the process sensing 322 can be implemented by software of the computing device 304.

Next, the computing device 304 executes a detecting phase 340, which includes a process defect detection 342, a layer defect detection 344, and a part defect detection 346. The detecting phase 340 identifies defects with respect to errors in the process (e.g., the process defect detection 342), defect within one or more layers (e.g., the layer defect detection 344), and defects across the component itself (e.g., the part defect detection 346). The detecting phase 340 and operations therein can be implemented by software of the computing device 304.

The computing device 304 also executes a reacting phase 350, which includes a feedback control 352, a scan path planning 354, and a decision making 356. The reacting phase 350 and operations therein can be implemented by software of the computing device 304. The results of the reacting 350 phase include corrective actions that are provided to the production operation 315. The corrected actions can include adjusting an area of interest to determine where to perform the in situ monitoring (e.g., by the feedback control 352), adjusting a scan path to accommodate or correct defects in the trending component 320 (e.g., by the scan path planning 354), and determining material deposit amounts to accommodate or correct defects in the trending component 320 (e.g., by the decision making 356). The production operation 315 is improved by the corrective actions from the computing device, such that the additive manufacturing machine 301 may now produce a desired component 350.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A material deposition process including in situ sensor analysis of a component in a formation state, the material deposition process implemented in part by an X-ray source and an X-ray detector of an additive manufacturing machine producing the component, the material deposition process comprising:
    sensing, by the X-ray source and the X-ray detector, in situ physical properties at an area of interest of the component during a three-dimensional object production, the X-ray source and the X-ray detector being axially offset from each other such that the X-ray source and the X-ray detector are not axially aligned with respect to the area of interest, wherein the in situ physical properties include hardness, local strain, yield strength, crystallite size, defect density, crystalline orientation, or texture;
    detecting compliance to specifications or defects in the in situ physical properties with respect to pre-specified material requirements;
    analyzing the defects to determine corrective actions; and
    implementing an updated three-dimensional object production, which includes the corrective actions, to complete the component.

2. The material deposition process of claim 1, the material deposition process comprising:
    implementing the three-dimensional object production of the component according to a computer design file.

3. The material deposition process of claim 1, the material deposition process comprising:
    feeding forward and back the corrective actions to the three-dimensional object production in real time to generate the updated three-dimensional object production.

4. The material deposition process of claim 1, wherein the X-ray source and the X-ray detector together acquire a full or partial X-ray diffraction signal or pattern that is analyzed to determine the in situ physical properties.

5. The material deposition process of claim 1, wherein the in situ physical properties additionally include density, porosity, or compositional variation.

6. The material deposition process of claim 1, wherein a compute device comprises a processor executing software to provide one or more process modeling, toolpath planning, defect detection, layer defect detection, part defect detection, feedback control, scan path planning, decision making, and process sensing operations for detecting the defects.

7. The material deposition process of claim 1, wherein a compute device comprises a database storing and providing the pre-specified material requirements and a computer design file for detecting the defects and implementing the three-dimensional object production.

* * * * *